United States Patent
Ye et al.

(10) Patent No.: US 10,072,135 B2
(45) Date of Patent: *Sep. 11, 2018

(54) COMPOSITIONS INCLUDING A POLYTHIOL, AN UNSATURATED COMPOUND, AND A DYE AND METHODS RELATING TO SUCH COMPOSITIONS

(71) Applicant: 3M INNOVATIVE PROPERTIES COMPANY, St. Paul, MN (US)

(72) Inventors: Sheng Ye, Woodbury, MN (US); Kathleen S. Shafer, Woodbury, MN (US); Michael S. Wendland, North St. Paul, MN (US); Jonathan D. Zook, Baytown Township, MN (US); Susan E. DeMoss, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 131 days.

This patent is subject to a terminal disclaimer.

(21) Appl. No.: 15/109,385

(22) PCT Filed: Dec. 19, 2014

(86) PCT No.: PCT/US2014/071688
§ 371 (c)(1),
(2) Date: Jun. 30, 2016

(87) PCT Pub. No.: WO2015/102967
PCT Pub. Date: Jul. 9, 2015

(65) Prior Publication Data
US 2016/0319106 A1    Nov. 3, 2016

Related U.S. Application Data

(60) Provisional application No. 61/921,744, filed on Dec. 30, 2013.

(51) Int. Cl.

| | |
|---|---|
| *C07D 277/82* | (2006.01) |
| *C08K 5/47* | (2006.01) |
| *C09J 11/06* | (2006.01) |
| *C09J 181/02* | (2006.01) |
| *G01N 21/25* | (2006.01) |
| *G01N 33/44* | (2006.01) |
| *C09B 29/033* | (2006.01) |
| *C08K 5/00* | (2006.01) |
| *G01N 21/17* | (2006.01) |

(52) U.S. Cl.
CPC .............. *C08K 5/47* (2013.01); *C07D 277/82* (2013.01); *C09J 11/06* (2013.01); *C09J 181/02* (2013.01); *G01N 21/25* (2013.01); *G01N 33/442* (2013.01); *C08K 5/0041* (2013.01); *C09B 29/0088* (2013.01); *G01N 2021/1748* (2013.01); *G01N 2021/1761* (2013.01)

(58) Field of Classification Search
None
See application file for complete search history.

(56) References Cited

U.S. PATENT DOCUMENTS

| | | | |
|---|---|---|---|
| 2,466,963 | A | 4/1949 | Patrick |
| 2,789,958 | A | 4/1957 | Fettes |
| 2,891,942 | A | 6/1959 | Merian |
| 3,207,614 | A | 9/1965 | Canevari |
| 3,382,296 | A | 5/1968 | Tenquist |
| 3,390,121 | A | 6/1968 | Burford |
| 3,773,706 | A | 11/1973 | Dunn, Jr. |
| 4,160,064 | A | 7/1979 | Nodiff |

(Continued)

FOREIGN PATENT DOCUMENTS

| | | |
|---|---|---|
| CN | 101328320 | 12/2008 |
| CN | 103113759 | 5/2013 |

(Continued)

OTHER PUBLICATIONS

Chen, "Synthesis and spectroscopic characterization of an alkoxysilane dye containing azo-benzothiazole chromophore for nonlinear optical applications", Dyes and Pigments, 2007, vol. 73, pp. 338-343.

(Continued)

*Primary Examiner* — Christopher Hixson
*Assistant Examiner* — Michelle Adams

(57) ABSTRACT

A curable composition having a polythiol; at least one unsaturated compound comprising two or more carbon-carbon double bonds, carbon-carbon triple bonds, or a combination thereof; and a dye compound represented by formula: A crosslinked composition prepared from the curable composition, a method for indicating curing in a curable composition, and a method of stabilizing a curable composition comprising a polythiol and at least one unsaturated compound comprising two or more carbon-carbon double bonds, carbon-carbon triple bonds, or a combination thereof are also disclosed.

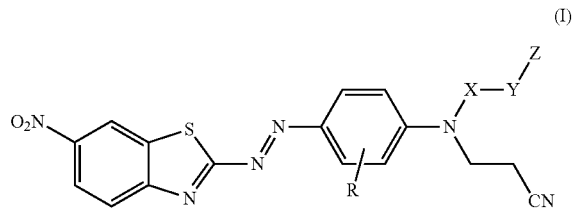

20 Claims, No Drawings

(56) References Cited

U.S. PATENT DOCUMENTS

| | | | |
|---|---|---|---|
| 4,164,492 A | 8/1979 | Cooper | |
| 4,165,425 A | 8/1979 | Bertozzi | |
| 4,232,136 A | 11/1980 | Kovacsay | |
| 4,241,166 A | 12/1980 | Klupfel | |
| 4,366,307 A | 12/1982 | Singh | |
| 4,370,428 A | 1/1983 | Danville | |
| 4,440,681 A | 4/1984 | Tappe | |
| 4,460,719 A | 7/1984 | Danville | |
| 4,467,079 A | 8/1984 | Hechenberger | |
| 4,522,963 A | 6/1985 | Kecskemethy | |
| 4,609,762 A | 9/1986 | Morris | |
| 4,734,101 A | 3/1988 | Himeno | |
| 5,225,472 A | 7/1993 | Cameron | |
| 5,302,627 A | 4/1994 | Field | |
| 5,387,488 A | 2/1995 | Kaneko | |
| 5,610,243 A | 3/1997 | Vietti | |
| 5,912,319 A | 6/1999 | Zook | |
| 5,933,559 A | 8/1999 | Petisce | |
| 5,958,584 A | 9/1999 | Petisce | |
| 5,959,071 A | 9/1999 | DeMoss | |
| 6,162,842 A | 12/2000 | Freche | |
| 6,172,179 B1 | 1/2001 | Zook | |
| 6,444,725 B1 | 9/2002 | Trom | |
| 6,447,708 B1 | 9/2002 | Thépot et al. | |
| 6,455,158 B1 | 9/2002 | Mei | |
| 6,465,544 B1 | 10/2002 | Bomal | |
| 6,509,418 B1 | 1/2003 | Zook | |
| 6,518,356 B1 | 2/2003 | Friese | |
| 6,778,753 B2 | 8/2004 | Blomquist | |
| 7,691,557 B2 | 4/2010 | Bachmann | |
| 7,871,446 B2 | 1/2011 | Jordan | |
| 9,772,321 B2 * | 9/2017 | Wendland | G01N 33/442 |
| 2003/0027903 A1 | 2/2003 | Nwoko | |
| 2003/0065069 A1 | 4/2003 | Wojciak | |
| 2003/0139488 A1 | 7/2003 | Wojciak | |
| 2003/0181546 A1 | 9/2003 | Hettich | |
| 2004/0247792 A1 | 12/2004 | Sawant | |
| 2006/0175005 A1 * | 8/2006 | Sawant | C08L 81/02 156/307.1 |
| 2006/0202158 A1 | 9/2006 | Chen | |
| 2007/0021526 A1 | 1/2007 | He | |
| 2010/0311184 A1 | 12/2010 | Diwu | |
| 2011/0171609 A1 | 7/2011 | Yang | |
| 2012/0040103 A1 | 2/2012 | Keledjian | |
| 2016/0032059 A1 * | 2/2016 | Ye | C08G 75/00 522/64 |
| 2016/0041143 A1 | 2/2016 | Wendland | |
| 2016/0319105 A1 | 11/2016 | Schultz | |

FOREIGN PATENT DOCUMENTS

| | | |
|---|---|---|
| DE | 206006 | 1/1984 |
| EP | 1095985 | 5/2001 |
| EP | 1308477 | 10/2002 |
| JP | 50-69381 | 6/1975 |
| JP | 59-120612 | 7/1984 |
| JP | 61-200170 | 4/1986 |
| JP | 62-034958 | 2/1987 |
| JP | H10-237335 | 8/1998 |
| JP | 2001-131436 | 5/2001 |
| JP | 2008-144103 | 6/2008 |
| WO | WO 2012-021781 | 2/2012 |
| WO | WO 2013-090988 | 6/2013 |
| WO | WO 2013-151893 | 10/2013 |
| WO | WO 2014-164103 | 10/2014 |
| WO | WO 2014-172305 | 10/2014 |
| WO | WO 2017-004015 | 5/2017 |

OTHER PUBLICATIONS

Cojocariu, "Synthesis and optical storage properties of a novel polymethacrylate with benzothiazole azo chromophore in the side chain", Journal of Materials Chemistry, 2004, vol. 14, pp. 2909-2916.

Peters, "Disperse Dyes: 4-Hetarylazo Derivatives from N-β-Cyanoethyl-N-β-Hydroxyethylaniline", Journal Chemical Technology Biotechnology 1992, vol. 53, pp. 301-308.

Peters, "Monoazo Disperse Dye Derived from Nitro-2-Aminobenzothiazoles", Dyes and Pigments, 1995, vol. 28, pp. 151-164.

Peters, "New Dyes and their Intermediates for Synthetic-polymer Fibres: III *-Halogenobenzothiazolylazo Dyes", Journal of the Society of Dyers and Colourists, 1969, vol. 85, pp. 507-509.

Sanchez, "Applications of advanced hybrid organic-inorganic nanomaterials: from laboratory to market", Chemical Society Reviews, 2011, vol. 40, pp. 696-753.

Towns, "Developments in azo disperse dyes derived from heterocyclic diazo components", Dyes and Pigments, 1999, vol. 42, pp. 3-28.

International Search Report for PCT International Application No. PCT/US2014/071688, dated Mar. 11, 2015, 4 pages.

* cited by examiner

COMPOSITIONS INCLUDING A POLYTHIOL, AN UNSATURATED COMPOUND, AND A DYE AND METHODS RELATING TO SUCH COMPOSITIONS

CROSS-REFERENCE TO RELATED APPLICATIONS

This application is a national stage filing under 35 U.S.C. 371 of PCT/US2014/071688, filed Dec. 19,2014 which claims priority to U.S. Provisional Application No. 61/921,744, filed Dec. 30, 2013, the disclosure of which is incorporated by reference in its entirety herein.

BACKGROUND

Inclusion of a dye in a curative or catalyst composition can be useful, for example, when the curative or catalyst must be admixed with a curable resin before placement and curing the resin. The dye can be useful, for example, for indicating that the curative or catalyst is uniformly mixed with the curable resin. Peroxide and dye formulations in which the color disappears when the peroxide is used to generate radicals during the cure of a curable resin are also known. See, for example, Japanese Pat. Appl. Kokai No. SHO 59-120612, published Jul. 21, 1984, and U.S. Pat. Appl. Pub. No. 2006/0202158 (Chen et al.). Although there are many ways to determine the extent of cure in cured systems, most methods require sampling and subsequent analysis of that sample using any of a number of techniques (e.g., spectroscopy, chromatography, and rheological measurements). These methods require equipment and may require interruption of a process since many of these methods cannot be performed while a manufacturing process is taking place. In addition, many of the analysis methods require a skilled user capable of interpreting results. Formulations including a dye and a catalyst or curative in which the color disappears upon curing provide a visual indication of cure, which does not require equipment or extensive interpretation.

SUMMARY

Compositions and methods according to the present disclosure include a dye compound that can be covalently incorporated into a cured composition including a polythiol and at least one unsaturated compound comprising two or more carbon-carbon double bonds, carbon-carbon triple bonds, or a combination thereof. Compositions containing such polythiols and unsaturated compounds are commonly referred to as thiol-ene or ene-thiol compositions and cure by free-radical initiated polymerization. The covalent incorporation of the dye compound eliminates the potential for dye components to bloom or leech out of the cured system. The dye provides a visible color change when free-radicals are generated in the compositions upon curing. Typically, and surprisingly, the dye compound also provides a free-radical inhibiting effect to prevent premature polymerization in the compositions disclosed herein.

In one aspect, the present disclosure provides a curable composition having a polythiol; at least one unsaturated compound comprising two or more carbon-carbon double bonds, carbon-carbon triple bonds, or a combination thereof; and a dye compound represented by formula:

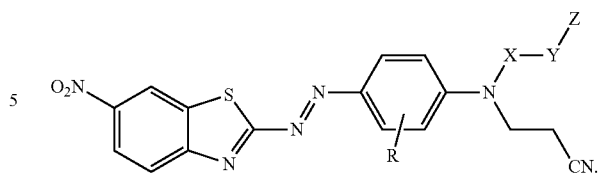

In another aspect, the present disclosure provides a cross-linked polymer network including a polythiol crosslinked with at least one unsaturated compound comprising two or more carbon-carbon double bonds, carbon-carbon triple bonds, or a combination thereof and a dye compound covalently incorporated into the crosslinked polymer network. The dye compound is represented by formula:

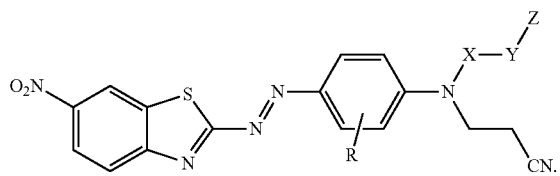

In another aspect, the present disclosure provides a method for indicating curing in a curable composition. The method includes providing the curable composition described above and allowing the composition to cure to provide a cured composition. The compound is present in the composition in an amount sufficient to provide the composition with a first absorbance at a wavelength in a range from 400 nanometers to 700 nanometers, and the cured composition has a second absorbance at the wavelength that is different from the first absorbance.

In another aspect, the present disclosure provides a method of stabilizing a curable composition comprising a polythiol and at least one unsaturated compound comprising two or more carbon-carbon double bonds, carbon-carbon triple bonds, or a combination thereof. The method includes adding to the composition a dye compound in an amount sufficient to reduce a viscosity increase of the curable composition relative to a comparative composition that is the same as the curable composition except that it does not contain the dye compound. The dye compound is represented by formula:

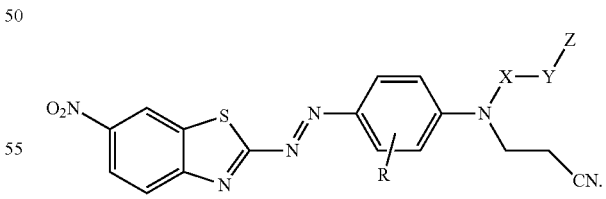

In any of the aforementioned aspects, R is hydrogen or alkyl, X is alkylene, Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and Z is an acrylate, a methacrylate, an acrylamide, a methacrylamide, a styrenyl, a terminal alkenyl, or a thiol in the dye compound.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The terms "cure" and "curable" refer to joining polymer chains together by covalent chemical bonds, usually via crosslinking molecules or groups, to form a network polymer. Therefore, in this disclosure the terms "cured" and "crosslinked" may be used interchangeably. A cured or crosslinked polymer is generally characterized by insolubility, but may be swellable in the presence of an appropriate solvent.

The term "polymer or polymeric" will be understood to include polymers, copolymers (e.g., polymers formed using two or more different monomers), oligomers or monomers that can form polymers, and combinations thereof, as well as polymers, oligomers, monomers, or copolymers that can be blended.

"Alkyl group" and the prefix "alk-" are inclusive of both straight chain and branched chain groups and of cyclic groups. In some embodiments, alkyl groups have up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms. Terminal "alkenyl" groups have at least 3 carbon atoms.

"Alkylene" is the multivalent (e.g., divalent or trivalent) form of the "alkyl" groups defined above.

"Arylalkylene" refers to an "alkylene" moiety to which an aryl group is attached. "Alkylarylene" refers to an "arylene" moiety to which an alkyl group is attached.

The terms "aryl" and "arylene" as used herein include carbocyclic aromatic rings or ring systems, for example, having 1, 2, or 3 rings and optionally containing at least one heteroatom (e.g., O, S, or N) in the ring optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Substituted styrene" includes alkyl, alkenyl, alkoxy, and halogen-substituted styrene.

All numerical ranges are inclusive of their endpoints and non-integral values between the endpoints unless otherwise stated (e.g., 1 to 5 includes 1, 1.5, 2, 2.75, 3, 3.80, 4, 5, etc.).

DETAILED DESCRIPTION

In some embodiments, the dye is represented by formula:

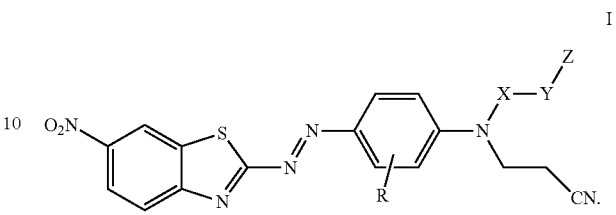

I

In formula I, R is hydrogen or alkyl. In some embodiments, R is hydrogen or alkyl having 1 to 4 carbon atoms (e.g., methyl, ethyl, n-propyl, isopropyl, n-butyl, isobutyl, or sec-butyl). In some embodiments, R is hydrogen.

In formula I, X is alkylene, in some embodiments, having from 1 to 6 or 2 to 6 carbon atoms. In some embodiments, X is —CH$_2$—CH$_2$—.

In formula I, Y is a bond, ether (i.e., —O—), thioether (i.e., —S—), amine (i.e., —NR$^1$—), amide (i.e., —N(R$^1$)—C(O)— or —C(O)—N(R$^1$)—), ester (i.e., —O—C(O)— or —C(O)—O—), thioester (i.e., —S—C(O)—, —C(O)—S—, —O—C(S)—, —C(S)—O—), carbonate (i.e., —O—C(O)—O—), thiocarbonate (i.e., —S—C(O)—O— or —O—C(O)—S—), carbamate (i.e., —(R$^1$)N—C(O)—O— or —O—C(O)—N(R$^1$)—, thiocarbamate (i.e., —N(R$^1$)—C(O)—S— or —S—C(O)—N(R$^1$)—), urea (i.e., —(R$^1$)N—C(O)—N(R$^1$)—), thiourea (i.e., —(R$^1$)N—C(S)—N(R$^1$)—) alkylene, arylalkylene, alkylarylene, or arylene, wherein alkylene, arylalkylene, alkylarylene, and arylene are optionally at least one of interrupted or terminated by at least one of an ether (i.e., —O—), thioether (i.e., —S—), amine (i.e., —NR$^1$—), amide (i.e., —N(R$^1$)—C(O)— or —C(O)—N(R$^1$)—), ester (i.e., —O—C(O)— or —C(O)—O—), thioester (i.e., —S—C(O)—, —C(O)—S—, —O—C(S)—, —C(S)—O—), carbonate (i.e., —O—C(O)—O—), thiocarbonate (i.e., —S—C(O)—O— or —O—C(O)—S—), carbamate (i.e., —(R$^1$)N—C(O)—O— or —O—C(O)—N(R$^1$)—, thiocarbamate (i.e., —N(R$^1$)—C(O)—S— or —S—C(O)—N(R$^1$)—, urea (i.e., —(R$^1$)N—C(O)—N(R$^1$)—), or thiourea (i.e., —(R$^1$)N—C(S)—N(R$^1$)—). In any of these groups that include an R$^1$, R$^1$ is hydrogen, alkyl, aryl, arylalkylenyl, or alkylarylenyl. In some embodiments, R$^1$ is hydrogen or alkyl, for example, having 1 to 4 carbon atoms (e.g., methyl, ethyl, n-propyl, isopropyl, n-butyl, isobutyl, or sec-butyl). In some embodiments, R$^1$ is methyl or hydrogen. The phrase "interrupted by at least one functional group" refers to having part of the alkylene, arylalkylene, or alkylarylene group on either side of the functional group. An example of an alkylene interrupted by an ether is —CH$_2$—CH$_2$—O—CH$_2$—CH$_2$—. The phrase "terminated" by at least one functional group refers to a functional group bonded at one end or the other of the alkylene, arylalkylene, alkylarylene, or arylene group. The terminal functional group may either be bonded to X or Z. In some embodiments, the terminal functional group is a —O—, —O—C(O)—, —O—C(O)—O—, —O—C(O)—NR$^1$— bonded to X. In some embodiments, Y is a bond, —O—, —O—C(O)—, —O—C(O)—NR$^1$—, or alkylene optionally at least one of interrupted or terminated by at least one ether, ester, carbonate, or carbamate. In some embodiments, Y is a bond. It should be understood that when Y is a bond, Z is bonded directly to X. In other words, Y is absent from formula I. In some embodiments, Y is —O—C(O)—. In some embodiments, Y is alkylene optionally at least one of interrupted or terminated by at least one ether or ester. In these embodiments, Y may be, for example, —O—CH$_2$—CH$_2$—O—CH$_2$—CH$_2$— or —CH$_2$CH$_2$—O—C(O)—C(CH$_3$)$_2$—.

In formula I, Z is a polymerizable group. It is typically a group that can undergo free-radical initiated polymerization. Z may be, for example, an acrylate, a methacrylate, an acrylamide, a methacrylamide, a styrenyl group, a terminal alkenyl, or a mercaptan. The terminal alkenyl may be a vinyl group (e.g., a vinyl ether when Y is terminated by —O—), or the terminal alkenyl may have at least three carbon atoms (e.g., allyl). In some embodiments, Z is acrylate, methacrylate, a mercaptan, or an acrylamide. In some embodiments, Z is acrylate or methacrylate. In some embodiments, Z is an acrylamide.

Compounds of formula I can be prepared, for example, beginning with an ester represented by formula X

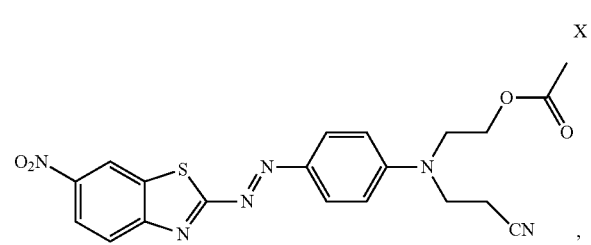 [SMILES: CC(=O)OCCN(CCC#N)c1ccc(/N=N/c2nc3ccc([N+](=O)[O-])cc3s2)cc1]

which is commercially available, for example, from Winchem Industrial Co. Ltd, China, and China Langchem Inc., China as "DISPERSE RED 177". This compound can be hydrolyzed under known saponification conditions to provide the hydroxyl compound, shown below as formula XI. Alternatively, compounds of formula I can be prepared by treating commercially available 2-amino-6-nitrobenzothiazole with nitrosyl sulfuric acid solution prepared in situ from sodium nitrite in concentrated sulfuric acid according to the method described in Cojocariu, C., et al. *J. Mater. Chem.*, 2004, vol. 14, pages 2909-2916. The reaction can conveniently be carried out in a mixture of dichloroacetic acid and glacial acetic acid after cooling below room temperature. The resultant diazonium sulfate salt can be coupled with N-(2-cyanoethyl)-N-(2-hydroxyethyl)aniline. Other alkyl-substituted N-(2-cyanoethyl)-N-(2-hydroxyalkyl)-anilines, which can be prepared by known methods, can also be useful in the coupling reaction.

The resultant compounds of formula XI:

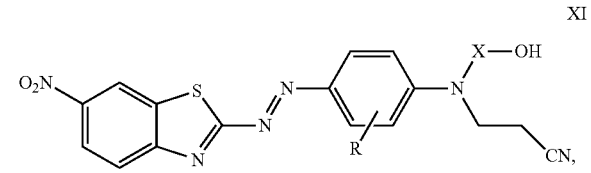

in which X and R are defined as in any of their embodiments described above, can be converted to compounds according to formula I using a variety of known synthetic methods. For example, the hydroxyl-group on the compound of formula XI can be converted to an acrylate or a methacrylate using acryloyl chloride or methacryloyl chloride, respectively, in the presence of a base to provide a compound of formula I in which Y is a bond, and Z is an acrylate or methacrylate group. Other esterification methods using acrylic acid, methacrylic acid, or equivalents thereof may be useful. The hydroxyl group in the compound of formula XI can also be reacted with a substituted or unsubstituted vinyl benzoic acid or an equivalent thereof under Mitsunobu reaction conditions to provide a compound in which Y is —O—C(O)— and Z is a styrene or substituted styrene. Conveniently the Mitsunobu coupling is carried out in the presence of triphenyl phosphine and diisopropyl azodicarboxylate or diethyl azodicarboxylate in a suitable solvent. The reaction can conveniently be carried out at or below ambient temperature. The hydroxyl group in the compound of formula XI can also be reacted with a vinyl-substituted azlactone to provide a compound of formula I in which Y is —O—C(O)-alkylene, and Z is an acrylamide group. The reaction can conveniently be carried out in the presence of a hindered amine. Compounds of formula XI can also be treated with isocyanatoalkyl acrylates or methacrylates or allyl isocyanate to provide compounds of formula I in which Y is a —O—C(O)—NR$^1$— or a —O—C(O)—NR$^1$-alkylene, and Z is an acrylate, methacrylate, or terminal alkenyl group. Such reactions can be carried out in the presence of tin compounds (e.g., dibutyltin dilaurate) at ambient temperature. The hydroxyl group can also be converted to an amine or thiol using standard functional group manipulation. The resultant amines or mercaptans can be reacted with carboxylic acids and equivalents thereof, azlactones, and isocyanates using known chemistry to provide a variety of Y and Z groups in the compounds of formula I. Further methods for the preparation of compounds of formula I can be found in the Examples, below.

In some embodiments, compositions according to the present disclosure in any of the embodiments described above and below include the compound of formula I in an amount from 0.1 percent to 0.00001 percent by weight, based on the total weight of the curable composition. In some embodiments, the compound of formula I is included in the composition in an amount from 0.05 percent to 0.00001 percent, from 0.04 percent to 0.0001 percent, or 0.02 percent to 0.001 percent by weight, based on the total weight of the curable composition.

A variety of polythiols and unsaturated compounds comprising two or more carbon-carbon double bonds, carbon-carbon triple bonds, or a combination thereof may be useful in the compositions according to the present disclosure. In some embodiments, the polythiol is monomeric. In these embodiments, the polythiol may be an alkylene, arylene, alkylarylene, arylalkylene, or alkylenearylalkylene having at least two mercaptan groups, wherein any of the alkylene, alkylarylene, arylalkylene, or alkylenearylalkylene are optionally interrupted by one or more ether (i.e., —O—), thioether (i.e., —S—), or amine (i.e., —NR$^1$—) groups and optionally substituted by alkoxy or hydroxyl. Useful monomeric polythiols may be dithiols or polythiols with more than 2 (in some embodiments, 3 or 4) mercaptan groups. In some embodiments, the polythiol is an alkylene dithiol in which the alkylene is optionally interrupted by one or more ether (i.e., —O—) or thioether (i.e., —S—) groups. Examples of useful dithiols include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane and mixtures thereof. Polythiols having more than two mercaptan groups include propane-1,2,3-trithiol; 1,2-bis[(2-mercaptoethyl)thio]-3-mercaptopropane; tetrakis(7-mercapto-2,5-dithiaheptyl)methane; and trithiocyanuric acid. Combination of any of these or with any of the dithiols mentioned above may be useful.

It should be understood that the unsaturated compound having carbon-carbon double bonds and/or carbon-carbon triple bonds are reactive and generally not part of an aromatic ring. In some of these embodiments, the carbon-carbon double and triple bonds are terminal groups in a linear aliphatic compound. However, styryl groups and allyl-substituted aromatic rings may be useful. The unsaturated compound may also include one or more ether (i.e., —O—), thioether (i.e., —S—), amine (i.e., —NR$^1$—), or ester (e.g., so that the compound is an acrylate or methacrylate) groups and one or more alkoxy or hydroxyl substituents. Suitable unsaturated compounds include dienes, diynes, divinyl ethers, diallyl ethers, ene-ynes, and trifunctional versions of any of these. Combinations of any of these groups may also be useful.

Examples of suitable vinyl ethers having two or more vinyl ether groups include divinyl ether, ethylene glycol divinyl ether, butanediol divinyl ether, hexanediol divinyl ether, diethylene glycol divinyl ether, triethylene glycol divinyl ether, tetraethylene glycol divinyl ether, cyclohexanedimethanol divinyl ether, polytetrahydrofuryl divinyl ether, trimethylolpropane trivinyl ether, pentaerythritol tetravinyl ether, and combinations of any of these. Useful divinyl ethers of formula $CH_2$=CH—O—(—R$^2$—O—)$_m$—CH=$CH_2$, in which R$^2$ is $C_2$ to $C_6$ branched alkylene can be prepared by reacting a polyhydroxy compound with acetylene. Examples of compounds of this type include compounds in which R$^2$ is an alkyl-substituted methylene group such as —CH(CH$_3$)— (e.g., those obtained from BASF, Florham Park, N.J., under the trade designation "PLURIOL", for which R$^2$ is ethylene and m is 3.8) or an alkyl-substituted ethylene (e.g., —CH$_2$CH(CH$_3$)— such as those obtained from International Specialty Products of Wayne, N.J., under the trade designation "DPE" (e.g., "DPE-2" and "DPE-3").

Other suitable examples of unsaturated compounds having at least two carbon-carbon double bonds or carbon-carbon triple bonds include triallyl-1,3,5-triazine-2,4,6-trione, 2,4,6-triallyloxy-1,3,5-triazine, 4-vinyl-1-cyclohexene, 1,5-cyclooctadiene, 1,6-heptadiyne, 1,7-octadiyne, and diallyl phthalate. When using polythiols having two thiol groups, a mixture of unsaturated compounds may be useful in which at least one unsaturated compound has two carbon-carbon double or triple bonds, and at least one unsaturated compound has at least three carbon-carbon double or triple bonds. Mixtures of unsaturated compounds having at least 5 percent functional equivalents of carbon-carbon double or triple bonds contributed by polyenes having at least three carbon-carbon double or triple bonds may be useful.

Typically the amounts of the polythiol(s) and unsaturated compound(s) are selected for the curable composition so that there is a stoichiometric equivalence of mercaptan groups and carbon-carbon double and triple bonds.

The compositions according to the present disclosure can be cured using free-radical polymerization. Accordingly, compositions according to the present disclosure typically include a free-radical initiator. Any free-radical initiator may be useful. Examples of suitable free-radical initiators include azo compounds (e.g., 2,2'-azobisisobutyronitrile (AIBN), 2,2'-azobis(2-methylbutyronitrile), or azo-2-cyanovaleric acid). In some embodiments, the free-radical initiator is an organic peroxide. Examples of useful organic peroxides include hydroperoxides (e.g., cumene, tert-butyl or tert-amyl hydroperoxide), dialkyl peroxides (e.g., di-tert-butylperoxide, dicumylperoxide, or cyclohexyl peroxide), peroxyesters (e.g., tert-butyl perbenzoate, tert-butyl peroxy-2-ethylhexanoate, tert-butyl peroxy-3,5,5-trimethylhexanoate, tert-butyl monoperoxymaleate, or di-tert-butyl peroxyphthalate), peroxycarbonates (e.g., tert-butylperoxy 2-ethylhexylcarbonate, tert-butylperoxy isopropyl carbonate, or di(4-tert-butylcyclohexyl) peroxydicarbonate), ketone peroxides (e.g., methyl ethyl ketone peroxide, 1,1-di(tert-butylperoxy)cyclohexane, 1,1-di(tert-butylperoxy)-3,3,5-trimethylcyclohexane, and cyclohexanone peroxide), and diacylperoxides (e.g., benzoyl peroxide or lauryl peroxide). The organic peroxide may be selected, for example, based on the temperature desired for use of the organic peroxide and compatibility with the curable composition. Combinations of two or more organic peroxides may also be useful.

The free-radical initiator may also be a photoinitiator. Examples of useful photoinitiators include benzoin ethers (e.g., benzoin methyl ether or benzoin butyl ether); acetophenone derivatives (e.g., 2,2-dimethoxy-2-phenylacetophenone or 2,2-diethoxyacetophenone); 1-hydroxycyclohexyl phenyl ketone; and acylphosphine oxide derivatives and acylphosphonate derivatives (e.g., bis(2,4,6-trimethylbenzoyl)phenylphosphine oxide, diphenyl-2,4,6-trimethylbenzoylphosphine oxide, isopropoxyphenyl-2,4,6-trimethylbenzoylphosphine oxide, or dimethyl pivaloylphosphonate). Many photoinitiators are available, for example, from BASF under the trade designation "IRGACURE". The photoinitiator may be selected, for example, based on the desired wavelength for curing and compatibility with the curable composition. When using a photoinitiator, the composition is typically curable using an actinic light source. In some embodiments, the composition is curable using a blue light source. In some embodiments, the composition is curable using a UV light source.

For any of the aforementioned embodiments, the compositions according to the present disclosure can be heated or exposed to light for a sufficient time to cure the composition.

In some embodiments, the polythiol in the curable composition according to the present disclosure is oligomeric or polymeric. Examples of useful oligomeric or polymeric polythiols include polythioethers and polysulfides. Polythioethers include thioether linkages (i.e., —S—) in their backbone structures. Polysulfides include disulfides linkages (i.e., —S—S—) in their backbone structures.

Polythioethers can be prepared, for example, by reacting dithiols with dienes, diynes, divinyl ethers, diallyl ethers, ene-ynes, or combinations of these under free-radical conditions. Useful dithiols include any of the dithiols, dienes, diynes, divinyl ethers, diallyl ethers, and ene-ynes listed above. Examples of useful polythioethers are described, for example, in U.S. Pat. Nos. 4,366,307 (Singh et al.), 4,609,762 (Morris et al.), 5,225,472 (Cameron et al.), 5,912,319 (Zook et al.), 5,959,071 (DeMoss et al.), 6,172,179 (Zook et al.), 6,509,418 (Zook et al.). In some embodiments, the polythioether is represented by formula HS—R$^3$—[S—(CH$_2$)$_2$—O—[—R$^4$—O—]$_m$—(CH$_2$)$_2$—S—R$^3$—]$_n$—SH, wherein each R$^3$ and R$^4$ is independently a $C_{2-6}$ alkylene, wherein alkylene may be straight-chain or branched, $C_{6-8}$ cycloalkylene, $C_{6-10}$ alkylcycloalkylene, —[(CH$_2$)$_p$—X—]$_q$—(—CH$_2$—)$_r$, in which at least one —CH$_2$— is optionally substituted with a methyl group, X is one selected from the group consisting of O, S and —NR$^5$—, R$^5$ denotes hydrogen or methyl, m is a number from 0 to 10, n is a number from 1 to 60, p is an integer from 2 to 6, q is an integer from 1 to 5, and r is an integer from 2 to 10. Polythioethers with more than two mercaptan groups may also be useful. Any of the free-radical initiators and methods described above may be useful for preparing the polythioethers. In some embodiments, the thermal initiators described above are combined with the dithiols with dienes, diynes, divinyl ethers, diallyl ethers, ene-ynes, or combinations of these, and the resulting mixture is heated to provide the polythioethers.

Polythioethers can also be prepared, for example, by reacting dithiols with diepoxides, which may be carried out by stirring at room temperature, optionally in the presence of a tertiary amine catalyst (e.g., 1,4-diazabicyclo[2.2.2]octane (DABCO)). Useful dithiols include any of those described above. Useful epoxides can be any of those having two epoxide groups. In some embodiments, the diepoxide is a bisphenol diglycidyl ether, wherein the bisphenol (i.e., —O—$C_6H_5$—$CH_2$—$C_6H_5$—O—) may be unsubstituted (e.g., bisphenol F), or either of the phenyl rings or the methylene group may be substituted by halogen (e.g., fluoro, chloro, bromo, iodo), methyl, trifluoromethyl, or hydroxymethyl. Polythioethers prepared from dithiols and diepoxides have pendent hydroxyl groups and can have structural repeating units represented by formula —S—$R^3$—S—$CH_2$—CH(OH)—$CH_2$—O—$C_6H_5$—$CH_2$—$C_6H_5$—O—$CH_2$—CH(OH)—$CH_2$—S—$R^3$—S—, wherein $R^3$ is as defined above, and the bisphenol (i.e., —O—$C_6H_5$—$CH_2$—$C_6H_5$—O—) may be unsubstituted (e.g., bisphenol F), or either of the phenyl rings or the methylene group may be substituted by halogen (e.g., fluoro, chloro, bromo, iodo), methyl, trifluoromethyl, or hydroxymethyl. Mercaptan terminated polythioethers of this type can be reacted with any of the dienes, diynes, divinyl ethers, diallyl ethers, and ene-ynes listed above under free radical conditions. Any of the free-radical initiators and methods described above may be useful for preparing the polythioethers. In some embodiments, the thermal initiators described above are used, and the resulting mixture is heated to provide the polythioethers.

The polythioethers may also be terminated with carbon-carbon double bonds, depending on the stoichiometry of the reaction. In these embodiments, the polythioethers can serve as the unsaturated compound having at least two carbon-carbon double bonds.

Polysulfides are typically prepared by the condensation of sodium polysulfide with bis-(2-chloroethyl) formal, which provides linear polysulfides having two terminal mercaptan groups. Branched polysulfides having three or more mercaptan groups can be prepared using trichloropropane in the reaction mixture. Examples of useful polysulfides are described, for example, in U.S. Pat. Nos. 2,466,963 (Patrick et al); 2,789,958 (Fettes et al); 4,165,425 (Bertozzi); and 5,610,243 (Vietti et al.). Polysulfides are commercially available under the trademarks "THIOKOL" and "LP" from Toray Fine Chemicals Co., Ltd., Urayasu, Japan and are exemplified by grades "LP-2", "LP-2C" (branched), "LP-3", "LP-33", and "LP-541".

Polythioethers and polysulfides can have a variety of useful molecular weights. In some embodiments, the polythioethers and polysulfides have number average molecular weights in a range from 500 grams per mole to 20,000 grams per mole, 1,000 grams per mole to 10,000 grams per mole, or 2,000 grams per mole to 5,000 grams per mole.

The polythioethers and polysulfides that are mercaptan-terminated may be combined with any of the unsaturated compounds including at least two carbon-carbon double or triple bonds described above using any of the free-radical initiators and methods described above to provide a cured composition according to the present disclosure.

Crosslinked networks prepared with polythiols and compounds having two or more carbon-carbon double bonds, carbon-carbon triple bonds, or a combination thereof as described above in any of their embodiments are useful for a variety of applications. For example, such crosslinked networks can be useful as sealants, for example, aviation fuel resistant sealants. Aviation fuel resistant sealants are widely used by the aircraft industry for many purposes. Principal among these uses are the sealing of integral fuel tanks and cavities, the sealing of the passenger cabin to maintain pressurization at high altitude, and for the aerodynamic smoothing of the aircraft's outer surfaces. Compositions according to the present disclosure may be useful in these applications, for example, because of their fuel resistance and low glass transition temperatures.

When used in sealant applications, for example, compositions according to the present disclosure can also contain fillers. Conventional inorganic fillers such as silica (e.g., fumed silica), calcium carbonate, aluminum silicate, and carbon black may be useful as well as low density fillers. In some embodiments, the composition according to the present disclosure includes at least one of silica, hollow ceramic elements, hollow polymeric elements, calcium silicates, calcium carbonate, or carbon black. Silica, for example, can be of any desired size, including particles having an average size above 1 micrometer, between 100 nanometers and 1 micrometer, and below 100 nanometers. Silica can include nanosilica and amorphous fumed silica, for example. Suitable low density fillers may have a specific gravity ranging from about 1.0 to about 2.2 and are exemplified by calcium silicates, fumed silica, precipitated silica, and polyethylene. Examples include calcium silicate having a specific gravity of from 2.1 to 2.2 and a particle size of from 3 to 4 microns ("HUBERSORB HS-600", J. M. Huber Corp.) and fumed silica having a specific gravity of 1.7 to 1.8 with a particle size less than 1 ("CAB-O-SIL TS-720", Cabot Corp.). Other examples include precipitated silica having a specific gravity of from 2 to 2.1 ("HI-SIL TS-7000"., PPG Industries), and polyethylene having a specific gravity of from 1 to 1.1 and a particle size of from 10 to 20 microns ("SHAMROCK S-395" Shamrock Technologies Inc.). The term "ceramic" refers to glasses, crystalline ceramics, glass-ceramics, and combinations thereof. Hollow ceramic elements can include hollow spheres and spheroids. The hollow ceramic elements and hollow polymeric elements may have one of a variety of useful sizes but typically have a maximum dimension of less than 10 millimeters (mm), more typically less than one mm. The specific gravities of the microspheres range from about 0.1 to 0.7 and are exemplified by polystyrene foam, microspheres of polyacrylates and polyolefins, and silica microspheres having particle sizes ranging from 5 to 100 microns and a specific gravity of 0.25 ("ECCOSPHERES", W. R. Grace & Co.). Other examples include alumina/silica microspheres having particle sizes in the range of 5 to 300 microns and a specific gravity of 0.7 ("FILLITE", Pluess-Stauffer International), aluminum silicate microspheres having a specific gravity of from about 0.45 to about 0.7 ("Z-LIGHT"), and calcium carbonate-coated polyvinylidene copolymer microspheres having a specific gravity of 0.13 ("DUALITE 6001AE", Pierce & Stevens Corp.). Such fillers, alone or in combination, can be present in a sealant in a range from 10 percent by weight to 55 percent by weight, in some embodiments, 20 percent by weight to 50 percent by weight, based on the total weight of the sealant composition.

When used in sealant applications, for example, compositions according to the present disclosure can also contain at least one of cure accelerators, surfactants, adhesion promoters, thixotropic agents, and solvents.

Sealants may optionally be used in combination with a seal cap, for example, over rivets, bolts, or other types of fasteners. A seal cap may be made using a seal cap mold, filled with a curable sealant, and placed over a fastener. The curable sealant may then be cured. In some embodiments, the seal cap and the curable sealant may be made from the same material. In some embodiments, the seal cap may be made from a curable composition disclosed herein. For more details regarding seal caps, see, for example, Int. Pat. Appl. Pub. No. WO2014/172305 (Zook et al.).

The dye compounds of formula I can be useful for indicating the extent of cure in the compositions according to the present disclosure. The compounds of formula I changes color in the presence of free-radicals, and thus can directly indicate cure by correlation of the concentration of free-radicals in the system. Compounds of formula I have an initial colored state and a less colored or colorless final state, as demonstrated in the examples, below.

Accordingly, the present disclosure also provides a method for indicating curing in a curable polymeric resin, including any of the curable polymeric resins described above. The method includes providing a composition comprising a curable polymeric resin, a free-radical initiator, and a compound of formula I in an amount sufficient to provide the composition with a first absorbance at a wavelength in a range from 400 nanometers to 700 nanometers. The wavelength may in a range, for example, from 450 nanometers to 650 nanometers, typically in a range from 500 nanometers to 550 nanometers. Allowing the composition to cure or curing the composition provides a cured composition that has a second absorbance at the wavelength that is different from the first absorbance. In some embodiments, the absorbance at the selected wavelength is decreased by at least 20, 25, 30, 35, 40, 45, or 50 percent or more. The initial and final absorbance can be measured, for example, using a UV/VIS spectrometer or a colorimeter. A composition having an absorbance at a wavelength in a range from 400 nanometers to 700 nanometers would typically be perceived by the human eye as a particular color. In some embodiments, a color in the composition is no longer visible in the cured composition. In these embodiments, a difference between the second absorbance and the first absorbance is visually determined. In some embodiments, providing the composition includes mixing the curable polymeric resin with a free-radical initiator and the compound of formula I. The free-radical initiator may be any of those described above. Mixing can be carried out until the visible color is uniformly dispersed in the composition, which may be useful in higher viscosity compositions.

In compositions that are light cured, the compositions according to the present disclosure also provide the advantage that they can indicate when they have been exposed to a curing light. In these cases, the disappearance or muting of the color can indicate that the compositions have been exposed to the curing light. The color change in the presently disclosed compositions indicates that free radicals have been generated. This feature can be beneficial when a manufacturing line has been stopped, for example, so that operators can easily differentiate exposed and unexposed compositions.

As shown in the Examples, below, while compositions that include certain photoinitiators can change color upon curing, there is typically a more visible color change when the dye compounds represented by formula I are present. For example, as shown in Table 2, below, compositions without the dye compound represented by formula I show low ΔE values (e.g, in a range from 5 to 12) before and after curing because the photoinitiator obtained from BASF under the trade designation "IRGACURE 819" bleaches color from yellow to colorless after exposure of the light. In contrast, Examples 1, 2, and 4, which include the dye compound of formula I show a higher ΔE value (e.g., typically greater than 30) before and after curing. The change from red to colorless upon curing of the compositions of the present disclosure provides an easily visible indication of curing.

Existing sealant products now in use in the aircraft industry are typically either two-part products or one-part products. For the two-part products, once the user mixes the two parts, the reaction begins and the sealant starts to form into an elastomeric solid. After mixing, the time that the sealant remains usable is called the application life. Throughout the application life, viscosity of the sealant gradually increases until the sealant is too viscous to be applied. Application life and cure time are typically related in that short application life products cure quickly. Conversely, long application life products cure slowly. In practice, customers choose products with differing application lives and cure times depending on the specific application. This requires the customer to maintain inventories of multiple products to address the production flow requirements of building and repairing aircraft. For one-part products, users can avoid a complicated mixing step, but the product has to be shipped and stored in a freezer before application. Advantageously, in many embodiments, compositions according to the present disclosure can be useful as one-part sealants that can simultaneously have a long application life but can be cured on demand.

As shown in the Examples below, compositions according to the present disclosure, which include a dye compound of formula I, are useful for preventing an increase in viscosity that is associated with polymerization in the composition before curing is desired. As shown in Table 1, a composition that includes 1,8-dimercapto-3,6-dioxaoctane, diethylene glycol divinyl ether, and triallylcyanurate increases in viscosity over 18 days from about 0.003 Pa-s to 59 Pa-s. In Example 2, when a dye compound of formula I is added to an otherwise identical composition, an increase in viscosity over 18 days from about 0.003 Pa-s to 1.65 Pa-s was observed. Surprisingly, the stabilization provided by the dye compound of formula I is better than the stabilization provided by a conventional free-radical inhibitor p-methoxy phenol (MEHQ). As shown in Comparative Example A, when MEHQ is added to a composition that includes 1,8-dimercapto-3,6-dioxaoctane, diethylene glycol divinyl ether, and triallylcyanurate, the composition increases in viscosity over 18 days from about 0.003 Pa-s to 11.5 Pa-s.

For convenience, the compositions according to the present disclosure may also include a solvent. The solvent can be any material capable of dissolving the compound of formula I (e.g., N-methyl-2-pyrrolidone, tetrahydrofuran, or ethyl acetate) or another component of the composition (e.g., a free-radical initiator). As shown in the Examples, below, when the dye compound represented by formula I is dissolved in N-methylpyrrolidinone before being added to the compositions according to the present disclosure, the color change and free-radical inhibition effects demonstrated in the resulting compositions are not as pronounced as when the dye compound of formula I is added as a solid. However, color change and free-radical inhibition are observed relative to a composition including no dye. See, for example, Example 3 in Tables 1 and 2. Accordingly, in some embodiments, compositions according to the present disclosure are free of N-methylpyrrolidinone. In some embodiments, the compositions according to the present disclosure are not prepared by adding the dye compound dissolved in N-methylpyrrolidinone to a polythiol and a compound comprising two or more carbon-carbon double bonds, carbon-carbon triple bonds, or a combination thereof. In some embodiments, compositions according to the present disclosure are free of solvent. In some embodiments, the compositions according to the present disclosure are not prepared by adding the dye compound dissolved in solvent to a polythiol and a compound comprising two or more carbon-carbon double bonds, carbon-carbon triple bonds, or a combination thereof.

As described above, the dye compound in the compositions according to the present disclosure is covalently bound into the curable composition and advantageously do not migrate out of the cured system over time. This can be advantageous, for example, if the cured compositions are exposed to aircraft fuel. Dye compounds covalently incorporated into the composition cannot be leeched out by such fuel exposure.

While a compound of formula I can be covalently incorporated into the curable compositions disclosed herein without losing its capability to becoming colorless upon curing, this is not true of all dyes. As reported in Int. Pat. Appl. Pub. No. WO2014/151708 (Wendland et al.), the addition of azo-2-naphthol dye Sudan III to 3M Premium Body Filler (3M part number 50597) and then subsequent curing showed the initial pink color disappeared around 6 minutes. However, when the Sudan III was converted into an acrylate and then incorporated into the body filler composition, no fading of the initial color was observed upon cure. In both cases, the body filler cured the same as when no dye was present. It is believed, the mechanism by which this dye goes colorless was disrupted by covalent incorporation of the polymerizable group into the dye structure.

Some Embodiments of the Disclosure

In a first embodiment, the present disclosure provides a curable composition comprising a polythiol; at least one unsaturated compound comprising two or more carbon-carbon double bonds, carbon-carbon triple bonds, or a combination thereof; and a dye compound represented by formula:

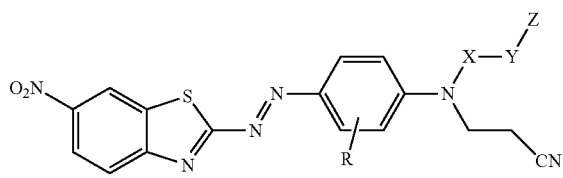

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and Z is an acrylate, a methacrylate, an acrylamide, a methacrylamide, a styrenyl, a terminal alkenyl, or a thiol.

In a second embodiment, the present disclosure provides the curable composition of the first embodiment, wherein R is hydrogen.

In a third embodiment, the present disclosure provides the curable composition of the first or second embodiment, wherein Z is an acrylamide, an acrylate, or a methacrylate.

In a fourth embodiment, the present disclosure provides the curable composition of any one of the first to third embodiments, wherein Y is a bond, —O—, —O—C(O)—, —O—C(O)—NR$^1$—, or alkylene optionally at least one of interrupted or terminated by at least one ether, ester, carbonate, or carbamate.

In a fifth embodiment, the present disclosure provides the curable composition of any one of the first to fourth embodiments, wherein Y is a bond, —O—C(O)—, or alkylene optionally at least one of interrupted or terminated by at least one ether or ester.

In a sixth embodiment, the present disclosure provides the curable composition of any one of the first to fifth embodiments, wherein —X—Y—Z is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C(CH$_3$)$_2$NHC(O)—CH=CH$_2$.

In a seventh embodiment, the present disclosure provides the curable composition of any one of the first to sixth embodiments, wherein the terminal alkenyl includes at least three carbon atoms.

In an eighth embodiment, the present disclosure provides the curable composition of any one of the first to seventh embodiments, further comprising a free-radical initiator.

In a ninth embodiment, the present disclosure provides the curable composition of the eighth embodiment, wherein the free-radical initiator is a photoinitiator.

In a tenth embodiment, the present disclosure provides the curable composition of the eighth embodiment, wherein the free-radical initiator is a thermal initiator.

In an eleventh embodiment, the present disclosure provides the curable composition of any one of the first to tenth embodiments, wherein the polythiol is monomeric.

In a twelfth embodiment, the present disclosure provides the curable composition of any one of the first to tenth embodiments, wherein the polythiol is oligomeric or polymeric.

In a thirteenth embodiment, the present disclosure provides the curable composition of the twelfth embodiment, wherein the polythiol is an oligomer or polymer prepared from components comprising a dithiol and a diene or divinyl ether.

In a fourteenth embodiment, the present disclosure provides the curable composition of any one of the first to thirteenth embodiments, wherein the at least one unsaturated compound comprises two carbon-carbon double bonds, and wherein the curable composition further comprises a second unsaturated compound comprising three carbon-carbon double bonds.

In a fifteenth embodiment, the present disclosure provides the curable composition of any one of the first to fourteenth embodiments, wherein the at least one unsaturated compound comprising two or more carbon-carbon double bonds, carbon-carbon triple bonds, or a combination thereof comprises at least one of a diene, a diyne, a divinyl ether, a diallyl ether, or an ene-yne.

In a sixteenth embodiment, the present disclosure provides the curable composition of any one of the first to fifteenth embodiments, further comprising at least one of silica, carbon black, calcium carbonate, or aluminum silicate.

In a seventeenth embodiment, the present disclosure provides a crosslinked polymer network comprising:

a polythiol crosslinked with at least one unsaturated compound comprising two or more carbon-carbon double bonds, carbon-carbon triple bonds, or a combination thereof; and a dye compound represented by the following formula covalently incorporated into the crosslinked polymer network:

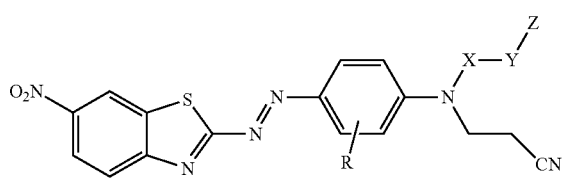

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, a terminal alkenyl, or a thiol,
wherein the crosslinked polymer network is prepared from the curable composition according to any one of the first to sixteenth embodiments.

In an eighteenth embodiment, the present disclosure provides a sealant comprising the crosslinked polymer network of the seventeenth embodiment.

In a nineteenth embodiment, the present disclosure provides a method for indicating curing in a curable composition, the method comprising:

providing the curable composition of any one of the first to sixteenth embodiments, wherein the compound is present in the composition in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

In a twentieth embodiment, the present disclosure provides the method of the nineteenth embodiment, wherein the difference between the first absorbance and the second absorbance is visually determined.

In a twenty-first embodiment, the present disclosure provides the method of the nineteenth or twentieth embodiment, wherein mixing is carried out until the composition is uniformly colored.

In a twenty-second embodiment, the present disclosure provides a method of stabilizing a curable composition comprising a polythiol and at least one unsaturated compound comprising two or more carbon-carbon double bonds, carbon-carbon triple bonds, or a combination thereof, the method comprising adding to the composition a dye compound of the following formula:

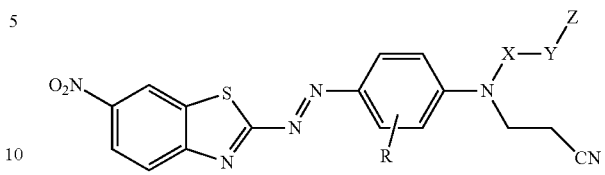

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, a terminal alkenyl, or a thiol,
in an amount sufficient to reduce a viscosity increase of the curable composition relative to a comparative composition that is the same as the curable composition except that it does not contain the dye compound.

In a twenty-third embodiment, the present disclosure provides the method of the twenty-second embodiment, wherein R is hydrogen.

In a twenty-fourth embodiment, the present disclosure provides the method of any one of the twenty-second to twenty-third embodiments, wherein Z is an acrylamide, an acrylate, or a methacrylate.

In a twenty-fifth embodiment, the present disclosure provides the method of any one of the twenty-second to twenty-fourth embodiments, wherein Y is a bond, —O—, —O—C(O)—, —O—C(O)—NR$^1$—, or alkylene optionally at least one of interrupted or terminated by at least one ether, ester, carbonate, or carbamate.

In a twenty-sixth embodiment, the present disclosure provides the method of any one of the twenty-second to twenty-fifth embodiments, wherein Y is a bond, —O—C(O)—, or alkylene optionally at least one of interrupted or terminated by at least one ether or ester.

In a twenty-seventh embodiment, the present disclosure provides the method of any one of the twenty-second to twenty-sixth embodiments, wherein —X—Y—Z is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C(CH$_3$)$_2$NHC(O)—CH=CH$_2$.

In a twenty-eighth embodiment, the present disclosure provides the method of any one of the twenty-second to twenty-seventh embodiments, wherein the terminal alkenyl includes at least three carbon atoms.

In a twenty-ninth embodiment, the present disclosure provides the method of any one of the twenty-second to twenty-eighth embodiments, further comprising a free-radical initiator.

In a thirtieth embodiment, the present disclosure provides the method of the twenty-ninth embodiment, wherein the free-radical initiator is a photoinitiator.

In a thirty-first embodiment, the present disclosure provides the method of the twenty-ninth embodiment, wherein the free-radical initiator is a thermal initiator.

In a thirty-second embodiment, the present disclosure provides the method of any one of the twenty-second to thirty-first embodiments, wherein the polythiol is monomeric.

In a thirty-third embodiment, the present disclosure provides the method of any one of the twenty-second to thirty-first embodiments, wherein the polythiol is oligomeric or polymeric.

In a thirty-fourth embodiment, the present disclosure provides the method of the thirty-third embodiment, wherein the polythiol is an oligomer or polymer prepared from components comprising a dithiol and a diene or divinyl ether.

In a thirty-fifth embodiment, the present disclosure provides the method of any one of the twenty-second to thirty-fourth embodiments, wherein the at least one unsaturated compound comprises two carbon-carbon double bonds, and wherein the curable composition further comprises a second unsaturated compound comprising three carbon-carbon double bonds.

In a thirty-sixth embodiment, the present disclosure provides the method of any one of the twenty-second to thirty-fifth embodiments, wherein the at least one unsaturated compound comprising two or more carbon-carbon double bonds, carbon-carbon triple bonds, or a combination thereof comprises at least one of a diene, a diyne, a divinyl ether, a diallyl ether, or an ene-yne.

In a thirty-seventh embodiment, the present disclosure provides the method of any one of the twenty-second to thirty-sixth embodiments, further comprising at least one of silica, carbon black, calcium carbonate, or aluminum silicate.

In order that this disclosure can be more fully understood, the following examples are set forth. It should be understood that these examples are for illustrative purposes only, and are not to be construed as limiting this disclosure in any manner.

EXAMPLES

The following abbreviations are used to describe the examples:
° C.: degrees Centigrade
cm: centimeter
g/cm$^3$ grams per cubic centimeter
LED: light emitting diode
mg: milligram
mil: 10$^{-3}$ inch
mL: milliliter
mm: millimeter
mmol: millimole
μL: microliter
μmol: micromole
nm: nanometer
NMR: nuclear magnetic resonance
Pa·s: Pascal second
T$_g$: glass transition temperature
W: Watt
Reagents.
Unless stated otherwise, all other reagents were obtained, or are available from fine chemical vendors, such as: Sigma-Aldrich Company, St. Louis, Mo.; EMD Millipore Chemicals, Billerica, Mass.; Alfa Aesar, Ward Hill, Mass.; J.T. Baker, Phillipsburg, N.J.; BDH Merck Ltd., Poole, Dorset, UK, and Cambridge Isotope Laboratories, Inc., Andover, Mass.; or may be synthesized by known methods. Unless otherwise reported, all ratios are by weight.

Abbreviations for reagents used in the examples are as follows:
Oligomer 1: A liquid polythioether oligomer prepared as follows. Into a 12-liter round bottom flask equipped with an air-driven stirrer, thermometer, and a dropping funnel, was added 4706 grams (25.8 moles) DMDO and 999 grams (3.0 moles) of a diglycidylether of bisphenol F, obtained under the trade designation "EPALLOY 8220" from Emerald Performance Materials, LLC, Cuyahoga Falls, Ohio; 1.7 g DABCO (0.02 weight percent) was mixed in as a catalyst. The system was flushed with nitrogen, then mixed and heated for four hours at 60° C. to 70° C. 150 g (0.6 mole) of triallylcyanurate was added along with approximate 0.4 g 2,2'-azobis(2-methylbutyronitrile), obtained under the trade designation "VAZO-67" from E.I. du Pont de Nemours and Company, Wilmington, Del. The material was mixed and heated at approximately 60° C. for 3 hrs. 3758 g (18.6 moles) triethyleneglycol divinylether, obtained under the trade designation "RAPI-CURE DVE-3" from Ashland Specialty Ingredients, Wilmington, Del. was then added drop-wise to the flask over 4 hours, keeping the temperature between 60° C. to 70° C. 2,2'-azobis(2-methylbutyronitrile) was added in approximately 0.4 g units over approximately 8 hours for a total of 1.2 g. The temperature was raised to 100° C. and the material degassed for approximately 1 hour. The resultant polythioether oligomer was approximately 3200 MW with 2.2 functionality.
CDCl$_3$: deuterated chloroform
DMDO: 1,8-Dimercapto-3,6-dioxaoctane, obtained from Arkena, Inc., King of Prussia, Pa.
d$_6$-DMSO: deuterated dimethyl sulfoxide
DVE: Diethyleneglycol divinyl ether, obtained from BASF Corp., Florham Park, N.J.
I-819: Phenylbis(2,4,6-trimethylbenzoyl)phosphine Oxide, obtained under the trade designation "IRGACURE 819" from BASF Corp.
MEHQ: p-methoxy phenol
TAC: Triallylcyanurate, obtained from Sartomer, Inc., Exton, Pa.

Synthesis of 3-{(2-hydroxy-ethyl)-[4-(6-nitro-benzothiazol-2-ylazo)-phenyl]-amino}-propionitrile:

5.00 grams (25.6 mmol) 2-amino-6-nitrobenzothiazole was added to 66 mL of a 5:1 (by volume) solution of dichloroacetic acid:glacial acetic acid in a 250 mL flask and dissolved by heating to 50° C. for 15 minutes. The solution was cooled to 0° C., then slowly added, with constant stirring over a 10 minute period, to a 250 mL flask containing a solution of 1.94 grams (28.1 mmol) sodium nitrite in 13 mL concentrated sulfuric acid held at 0° C. After stirring for an additional 30 minutes, this solution was slowly added to a 250 mL flask containing a mixture of 4.20 grams (22.1 mmol) N-(2-cyanoethyl)-N-(2-hydroxyethyl)aniline in 13 mL acetic acid, also held at 0° C., and stirred for 1 hour. The reaction mixture was then neutralized by the addition of a saturated aqueous sodium carbonate solution until the pH of the reaction mixture was approximately 7, and the resulting precipitate isolated by vacuum filtration. The precipitate was dissolved in 200 mL methylene chloride, then dried by passing through a bed of anhydrous sodium sulfate, filtered, and condensed in a rotary evaporator. The resulting solid was further purified by loading onto a 3 by 23 cm silica gel column, then eluting with an acetone:methylene chloride solution where the solvent ratio, by volume, was gradually changed from 10:90 to 30:70. Subsequent fractions containing the pure compound were combined, condensed under reduced pressure and then dried under a vacuum of 0.3 mm mercury (40.0 Pa) at approximately 21° C. to yield 4.30 grams of a purple solid, subsequently confirmed by NMR spectroscopy to be 3-{(2-hydroxy-ethyl)-[4-(6-nitro-benzothiazol-2-ylazo)-phenyl]-amino}-propionitrile [$^1$H NMR (500 MHz, d$_6$-DMSO) δ 9.07 (d, J=2.4 Hz, 1H), 8.32 (dd, J=2.4, 8.9 Hz, 1H), 8.17 (d, J=8.9 Hz, 1H), 7.91 (d, J=9.4 Hz, 2H), 7.11 (d, J=9.4 Hz, 2H), 4.99 (t, J=5.1 Hz, 1H), 3.95 (t, J=7.1 Hz, 2H), 3.69 (m, 4H), 2.91 (t, J=6.9 Hz, 2H)].

Preparation 1

Synthesis of 2-methyl-acrylic acid 2-{(2-cyano-ethyl)-[4-(6-nitro-benzothiazol-2-ylazo)-phenyl]-amino}-ethyl ester

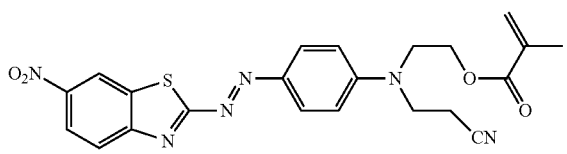 [SMILES: C=C(C)C(=O)OCCN(CCC#N)c1ccc(/N=N/c2nc3ccc([N+](=O)[O-])cc3s2)cc1]

0.29 mL (2.1 mmol) triethylamine was added to a 50 mL flask containing a solution of 0.55 grams (1.39 mmol) 3-{(2-hydroxy-ethyl)-[4-(6-nitro-benzothiazol-2-ylazo)-phenyl]-amino}-propionitrile in 20 mL tetrahydrofuran at approximately 21° C., after which it was cooled to 0° C. 162 μL (1.67 mmol) methacryloyl chloride was then added, and the mixture stirred under an atmosphere of nitrogen for 16 hours while the temperature was maintained at 0° C. The reaction mixture was filtered, and the filtrate condensed in a rotary evaporator. The resulting purple material was dissolved in chloroform, washed twice with a saturated sodium carbonate solution, washed twice with deionized water and washed once with a saturated sodium chloride solution. The organic portion was then dried by passing through a bed of anhydrous sodium sulfate, filtered, and condensed in a rotary evaporator. The resulting solid was further purified by loading onto an 3 by 23 cm silica gel column, then eluting with a methyl tert-butyl ether:methylene chloride solution where the solvent ratio, by volume, was gradually changed from 4:96 to 10:90. Subsequent fractions containing the pure compound were combined, condensed under reduced pressure and then dried under a vacuum of 0.3 mm mercury (40.0 Pa) at approximately 21° C. to yield 190 mg of a solid subsequently confirmed by NMR spectroscopy to be 2-methyl-acrylic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.84 (d, J=2.3 Hz, 1H), 8.40 (dd, J=2.3, 9.0 Hz, 1H), 8.23 (d, J=9.0 Hz, 1H), 8.11 (d, J=9.3 Hz, 2H), 6.93 (d, J=9.4 Hz, 2H), 6.15 (m, 1H), 5.68 (m, 1H), 4.49 (t, J=5.9 Hz, 2H), 3.98 (m, 4H), 2.82 (t, J=6.9 Hz, 2H), 1.99 (m, 3H)].

Preparation 2

Synthesis of acrylic acid 2-{(2-cyano-ethyl)-[4-(6-nitro-benzothiazol-2-ylazo)-phenyl]-amino}-ethyl ester

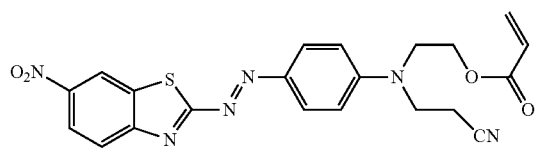 [SMILES: C=CC(=O)OCCN(CCC#N)c1ccc(/N=N/c2nc3ccc([N+](=O)[O-])cc3s2)cc1]

422 μL (3.03 mmol) triethylamine was added to a 100 mL flask containing a solution of 0.399 grams (1.01 mmol) 3-{(2-hydroxy-ethyl)-[4-(6-nitro-benzothiazol-2-ylazo)-phenyl]-amino}-propionitrile in 20 mL N,N-dimethyl formamide at approximately 21° C. This solution was stirred under an atmosphere of nitrogen for 10 minutes at approximately 21° C. 195 μL (2.41 mmol) acryloyl chloride was then added. The flask was placed in an oil bath, and the mixture was stirred under an atmosphere of nitrogen for 18 hours while the temperature was maintained at approximately 70° C. The reaction mixture was then partitioned between water (approximately 50 mL) and methylene chloride (approximately 50 mL). The aqueous layer was made basic by adding 5 mL of a saturated aqueous sodium bicarbonate solution. The organic layer was then removed, and the aqueous layer was extracted twice more with methylene chloride (approximately 50 mL each time). The organic layers were combined, dried by passing through a bed of anhydrous sodium sulfate, filtered, and condensed in a rotary evaporator. The resulting solid was further purified by loading onto an 4 by 30 cm silica gel column, then eluting with an approximately 5:95 (by volume) ethyl acetate:methylene chloride solution. Subsequent fractions containing the pure compound were combined, condensed under reduced pressure and then dried under a vacuum of 0.3 mm mercury (40.0 Pa) at approximately 21° C. to yield 280 mg of a solid subsequently confirmed by NMR spectroscopy to be acrylic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.78 (d, J=2.2 Hz, 1H), 8.34 (dd, J=2.2, 8.9 Hz, 1H), 8.17 (d, J=8.9 Hz, 1H), 8.06 (m, 2H), 6.86 (m, 2H), 6.42 (dd, J=1.2, 17.3 Hz, 1H), 6.11 (dd, J=10.5, 17.3 Hz, 1H), 5.89 (dd, J=1.2, 10.5 Hz, 1H), 4.43 (t, J=5.8 Hz, 2H), 3.91 (t, J=6.8 Hz, 2H), 3.90 (t, J=5.8 Hz, 2H), 2.75 (t, J=6.8 Hz, 2H)].

Preparation 3

Synthesis of 2-acryloylamino-2-methyl-propionic acid 2-{(2-cyano-ethyl)-[4-(6-nitro-benzothiazol-2-ylazo)-phenyl]-amino}-ethyl ester

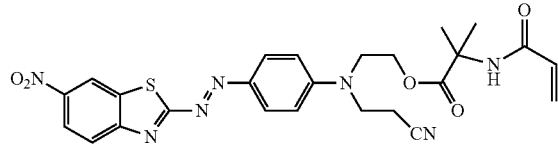 [SMILES: C=CC(=O)NC(C)(C)C(=O)OCCN(CCC#N)c1ccc(/N=N/c2nc3ccc([N+](=O)[O-])cc3s2)cc1]

540 μL (4.04 mmol) vinyl dimethylazlactone was added to a 100 mL flask containing a solution of 0.399 grams (1.01 mmol) 3-{(2-hydroxy-ethyl)-[4-(6-nitro-benzothiazol-2-ylazo)-phenyl]-amino}-propionitrile in 30 mL N,N-dimethyl formamide at approximately 21° C. 15 μL (101 μmol) 1,8-diazabicyclo[5.4.0]undec-7-ene was then added. The mixture was stirred under an atmosphere of nitrogen for 18 hours at approximately 21° C. The reaction mixture was then partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, condensed in a rotary evaporator, and then dried under a vacuum of 0.3 mm mercury (40.0 Pa) at approximately 21° C. to yield 465 mg of a solid subsequently confirmed by NMR spectroscopy to be 2-acryloylamino-2-methyl-propionic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.78 (d, J=2.2 Hz, 1H), 8.35 (dd, J=2.2, 8.9 Hz, 1H), 8.16 (d, J=8.9 Hz, 1H), 8.05 (m, 2H), 6.84 (m, 2H), 6.28 (dd, J=1.3, 17.0 Hz, 1H), 6.06 (dd, J=10.8, 17.0 Hz, 1H), 5.86 (s, 1H), 5.68 (dd, J=1.3, 10.8 Hz, 1H), 4.41 (t, J=5.6 Hz, 2H), 3.92 (t, J=7.0 Hz, 2H), 3.87 (t, J=5.6 Hz, 2H), 2.75 (t, J=7.0 Hz, 2H), 1.53 (s, 6H)].

Preparation 4

Synthesis of 4-vinyl-benzoic acid 2-{(2-cyano-ethyl)-[4-(6-nitro-benzothiazol-2-ylazo)-phenyl]-amino}-ethyl ester

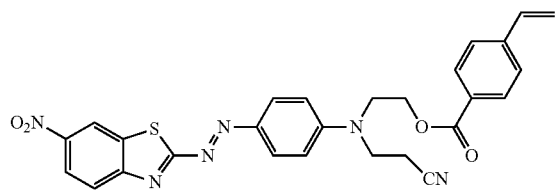 [SMILES: C=Cc1ccc(C(=O)OCCN(CCC#N)c2ccc(/N=N/c3nc4ccc([N+](=O)[O-])cc4s3)cc2)cc1]

0.199 grams (503 μmol) 3-{(2-hydroxy-ethyl)-[4-(6-nitro-benzothiazol-2-ylazo)-phenyl]-amino}-propionitrile, 57.6 mg (389 μmol) 4-vinyl benzoic acid and 0.229 grams triphenylphosphine were dissolved in 10 mL tetrahydrofuran in a 100 mL flask at approximately 21° C. This solution was cooled to 0° C. by placing the flask in an ice/water bath. The flask was equipped with an addition funnel containing a solution of 265 μL (1.35 mmol) diisopropyl azodicarboxylate (DIAD) in 5 mL of tetrahydrofuran (THF). The DIAD/THF solution was added dropwise to the stirred reaction mixture over a period of 30 minutes under an atmosphere of nitrogen while the temperature was maintained at approximately 0° C. When the addition was complete, the reaction mixture was allowed to warm to approximately 21° C. The reaction mixture was then stirred under an atmosphere of nitrogen for 18 hours at approximately 21° C. The reaction mixture was condensed in a rotary evaporator. The resulting material was partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, and condensed in a rotary evaporator. The resulting solid was further purified by loading onto an 4 by 20 cm silica gel column, then eluting with an approximately 5:95 (by volume) ethyl acetate:methylene chloride solution. Subsequent fractions containing the pure compound were combined, condensed under reduced pressure and then dried under a vacuum of 0.3 mm mercury (40.0 Pa) at approximately 21° C. to yield 143 mg of a solid subsequently confirmed by NMR spectroscopy to be 4-vinyl-benzoic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.71 (d, J=2.2 Hz, 1H), 8.29 (dd, J=2.2, 8.9 Hz, 1H), 8.12 (d, J=8.9 Hz, 1H), 8.00 (m, 2H), 7.92 (m, 2H), 7.44 (m, 2H), 6.88 (m, 2H), 6.71 (dd, J=10.7, 17.6 Hz, 1H), 5.85 (d, J=17.6 Hz, 1H), 5.37 (d, J=10.7 Hz, 1H), 4.57 (t, J=5.8 Hz, 2H), 3.99 (t, J=5.8 Hz, 2H), 3.93 (t, J=6.8 Hz, 2H), 2.77 (t, J=6.8 Hz, 2H)].

Preparation 5

Synthesis of allyl-carbamic acid 2-{(2-cyano-ethyl)-[4-(6-nitro-benzothiazol-2-ylazo)-phenyl]-amino}-ethyl ester

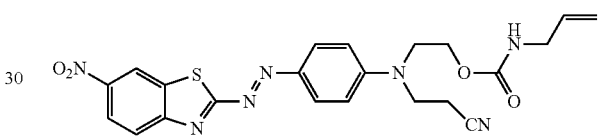

180 μL (2.04 mmol) allyl isocyanate was added to a 20 mL vial containing a solution of 0.200 grams (505 μmol) 3-{(2-hydroxy-ethyl)-[4-(6-nitro-benzothiazol-2-ylazo)-phenyl]-amino}-propionitrile in 10 mL N,N-dimethyl formamide at approximately 21° C. 30 μL (505 μmol) dibutyltin dilaurate was then added. The vial was capped and mixed in a mechanical shaker, model "WRIST ACTION SHAKER MODEL 75" from Burrell Scientific, Pittsburgh, Pa., for 18 hours at approximately 21° C. The reaction mixture was then partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, condensed in a rotary evaporator, and then dried under a vacuum of 1.0 mm mercury (133.3 Pa) at approximately 90° C. to yield 260 mg of a solid subsequently confirmed by NMR spectroscopy to be allyl-carbamic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.68 (d, J=2.2 Hz, 1H), 8.26 (dd, J=2.2, 9.0 Hz, 1H), 8.09 (d, J=9.0 Hz, 1H), 7.89 (m, 2H), 6.81 (m, 2H), 5.78 (m, 1H), 5.14 (d, J=17.3 Hz, 1H), 5.10 (d, J=10.2 Hz, 1H), 4.94 (t, J=5.5 Hz, 1H), 4.33 (t, J=5.6 Hz, 2H), 3.86 (t, J=6.8 Hz, 2H), 3.83 (t, J=5.6 Hz, 2H), 2.75 (t, J=6.8 Hz, 2H)].

Polythioether 1 (PTE-1)

A curable polythioether composition was prepared as follows. A 40 ml. amber glass vial was charged with 5.000 grams DMDO, 3.7229 grams DVE, 0.0937 grams I-819 and 0.6473 grams TAC at 21° C. The vial was then sealed and placed on a laboratory roll mill for 10 minutes until the I-819 had dissolved.

Polythioether 2 (PTE-2)

A curable polythioether composition was prepared as follows. A 40 ml. amber glass vial was charged with 5.000 grams DMDO, 3.1067 grams DVE, 0.0940 grams I-819 and 1.2946 grams TAC at 21° C. The vial was then sealed and placed on a laboratory roll mill for 10 minutes until the I-819 had dissolved.

Polythioether 3 (PTE-3)

A curable polythioether composition was prepared as follows. A 40 ml. amber glass vial was charged with 10.0000 grams Oligomer 1, 0.1088 grams I-819 and 0.8794 grams TAC at 21° C. The vial was then sealed and placed on a laboratory roll mill for 8 hours until the I-819 had dissolved.

Example 1

A sample of PTE-1 was prepared as described above, wherein 0.0015 grams 2-acryloylamino-2-methyl-propionic acid 2-{(2-cyano-ethyl)-[4-(6-nitro-benzothiazol-2-ylazo)-phenyl]-amino}-ethyl ester was added to the amber vial following the addition of I-819. The vial was then sealed and placed on a laboratory roll mill for 24 hours until the dye and I-819 dissolved.

Example 2

A sample of PTE-2 was prepared as described above, wherein 0.0005 grams 2-acryloylamino-2-methyl-propionic acid 2-{(2-cyano-ethyl)-[4-(6-nitro-benzothiazol-2-ylazo)-phenyl]-amino}-ethyl ester was added to the amber vial following the addition of I-819. The vial was then sealed and placed on a laboratory roll mill for 24 hours until the dye and I-819 dissolved.

Example 3

A sample of PTE-2 was prepared as described above, wherein 100 µL of a 0.005% by weight solution of 2-acryloylamino-2-methyl-propionic acid 2-{(2-cyano-ethyl)-[4-(6-nitro-benzothiazol-2-ylazo)-phenyl]-amino}-ethyl ester in N-methylpyrrolidinone was added to the amber vial following the addition of I-819. The vial was then sealed and placed on a laboratory roll mill for 10 minutes until the dye and I-819 dissolved.

Example 4

The procedure generally described in Example 3 was repeated, wherein the PTE-2 was substituted with an equal weight of PTE-3. The roll milling continued for 8 hours until the dye and I-819 dissolved.

Comparative Example A

The procedure generally described in Example 2 was repeated, wherein the 2-acryloylamino-2-methyl-propionic acid 2-{(2-cyano-ethyl)-[4-(6-nitro-benzothiazol-2-ylazo)-phenyl]-amino}-ethyl ester was substituted by an equal weight of MEHQ. The vial was then sealed and placed on a laboratory roll mill for 24 hours until the I-819 dissolved.

Test Methods

The following test methods were used to evaluate the stability of the uncured samples and the color change upon curing.

Stability.

Uncured resin stability, as a function of change in dynamic viscosity, was measured for PTE-2, and the corresponding Examples 2, 3 and Comparative A, after 18 days at 21° C. in the amber vials. Results listed in Table 1 were measured using a model "AR2000" rheometer, obtained from TA Instruments, New Castle, Del.

Samples were poured into a nominally 2 by 2 by 0.2 cm silicone rubber mold and cured by exposure at 21° C., for 30 seconds at a distance of 1.27 cm, to a 455 nm LED, using a model "CF2000" controller, obtained from Clearstone Technologies, Inc., Minneapolis, Minn.

Color Measurement

The change in color upon curing, as defined by ΔE values, was measured using a colorimeter, such as a model "MINISCAN XE PLUS D/8S" or "MINISCAN EZ", in mode D65/10*, obtained from Hunter Associates Laboratory, Inc., Reston, Va. Results are listed in Table 2.

Tg:

The glass transition temperature of cured polythioether resins PTE-1 and PTE-3, and the corresponding Examples 1 and 4, was measured using a model "DSC Q2000" differential scanning calorimeter, obtained from TA Instruments. Results are listed in Table 3.

Jet Fuel Resistance

Cured polythioether resins PTE-1 and PTE-3, and corresponding Examples 1 and 4, were also evaluated for jet fuel resistance, according to Society of Automotive Engineers (SAE) International Standard AS5127/1. The cured materials were immersed in Jet Reference Fluid Type 1 (JRF1) for 7 days at 60° C., after which % swell and % weight gain of the sample were determined JRF1 composition is defined by SAE Standard AMS2629. Results are listed in Table 3.

TABLE 1

| Sample | Hold Time (Days) | Shear Stress (Pa) | Dynamic Viscosity (Pa · s) |
|---|---|---|---|
| PTE-2 | 0 | ~10 | 0.003~0.005 |
| PTE-2 | 18 | 9.997 | 59.00 |
| Example 2 | 18 | 9.888 | 1.65 |
| Example 3 | 18 | 9.984 | 11.46 |
| Comparative A | 18 | 9.973 | 6.83 |

TABLE 2

| Sample | Days Stored[a] | Curing Step | L* | a* | b* | ΔE |
|---|---|---|---|---|---|---|
| PTE-1 | 0 | Before | 64.25 | −6.30 | 12.23 | 20.40 |
|  |  | After | 82.58 | −3.08 | 3.86 |  |
| Example 1 | 71 | Before | 39.54 | 49.07 | 12.11 | 68.90 |
|  |  | After | 82.06 | −5.10 | 9.83 |  |
| PTE-2 | 18 | Before | 83.71 | −10.73 | 18.13 | 12.79 |
|  |  | After | 84.00 | −4.74 | 6.83 |  |
| Example 2 | 18 | Before | 62.28 | 23.29 | 11.91 | 34.89 |
|  |  | After | 83.00 | −4.57 | 7.63 |  |
| Comparative A | 18 | Before | 83.49 | −10.47 | 17.36 | 12.92 |
|  |  | After | 83.26 | −4.33 | 5.99 |  |
| Example 3 | 18 | Before | 79.46 | −5.08 | 17.03 | 10.83 |
|  |  | After | 82.96 | −4.44 | 6.81 |  |
| PTE-3 | 0 | Before | 80.42 | −7.13 | 29.63 | 15.63 |
|  |  | After | 80.88 | −2.10 | 14.83 |  |
| Example 4 | 0 | Before | 41.21 | 56.44 | 23.02 | 64.33 |
|  |  | After | 76.63 | 3.46 | 14.22 |  |

[a]Number of days a sample was stored before evaluation.

TABLE 3

| Sample | Tg (° C.) | Density (g/cm³) | Jet Fuel Resistance | | |
|---|---|---|---|---|---|
| | | | Swell (%) | Weight Gain (%) | Weight Loss (%) |
| PTE-1 | −63 | 1.19 | 20.6 | 13.5 | 4.4 |
| Example 1 | −63 | 1.16 | 15.5 | 9.1 | 10.5 |
| PTE-3 | −55 | 1.18 | 17.9 | 12.7 | 6.8 |
| Example 4 | −56 | 1.16 | 15.6 | 11.6 | 1.4 |

Various modifications and alterations of this disclosure may be made by those skilled the art without departing from the scope and spirit of the disclosure, and it should be understood that this invention is not to be unduly limited to the illustrative embodiments set forth herein.

What is claimed is:

1. A curable composition comprising a polythiol; at least one unsaturated compound comprising two or more carbon-carbon double bonds, carbon-carbon triple bonds, or a combination thereof; and a dye compound represented by formula:

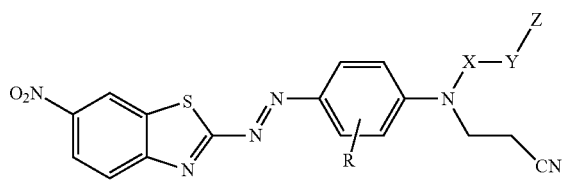

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, a terminal alkenyl, or a thiol.

2. The curable composition of claim 1, wherein Z is an acrylamide, an acrylate, or a methacrylate.

3. The curable composition of claim 1, wherein Y is a bond, —O—, —O—C(O)—, —O—C(O)—NR$^1$—, or alkylene optionally at least one of interrupted or terminated by at least one ether, ester, carbonate, or carbamate.

4. The curable composition of claim 3, wherein —X—Y—Z is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C(CH$_3$)$_2$NHC(O)—CH=CH$_2$.

5. The curable composition of claim 1, further comprising a free-radical initiator.

6. The curable composition of claim 5, wherein the free-radical initiator is a photoinitiator.

7. The curable composition of claim 5, wherein the free-radical initiator is a thermal initiator.

8. The curable composition of claim 1, wherein the polythiol is monomeric.

9. The curable composition of claim 1, wherein the polythiol is oligomeric or polymeric.

10. The curable composition of claim 9, wherein the polythiol is an oligomer or polymer prepared from components comprising a dithiol and a diene or divinyl ether.

11. The curable composition of claim 1, wherein the at least one unsaturated compound comprises two carbon-carbon double bonds, and wherein the curable composition further comprises a second unsaturated compound comprising three carbon-carbon double bonds.

12. The curable composition of claim 1, further comprising at least one of silica, carbon black, calcium carbonate, or aluminum silicate.

13. The curable composition of claim 1, wherein the at least one unsaturated compound comprising two or more carbon-carbon double bonds, carbon-carbon triple bonds, or a combination thereof comprises at least one of a diene, a diyne, a divinyl ether, a diallyl ether, or an eneyne.

14. The curable composition of claim 1, wherein the terminal alkenyl includes at least three carbon atoms.

15. The curable composition of claim 1, wherein Y is a bond, —O—C(O)—, or alkylene optionally at least one of interrupted or terminated by at least one ether or ester.

16. The curable composition of claim 1, wherein R is hydrogen.

17. A crosslinked polymer network comprising:
a polythiol crosslinked with at least one unsaturated compound comprising two or more carbon-carbon double bonds, carbon-carbon triple bonds, or a combination thereof; and
a dye compound represented by the following formula covalently incorporated into the crosslinked polymer network:

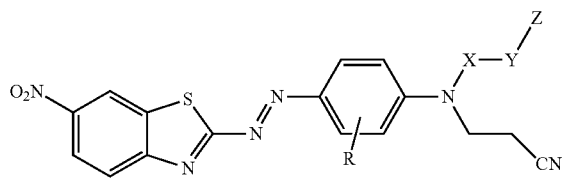

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, a terminal alkenyl, or a thiol, wherein Z has been reacted to form a covalent bond in the crosslinked polymer network.

18. A sealant comprising the crosslinked polymer network of claim 17.

19. A method for indicating curing in a curable composition, the method comprising:
providing the curable composition of claim 1, wherein the dye compound is present in the composition in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

20. A method of stabilizing a curable composition comprising a polythiol and at least one unsaturated compound comprising two or more carbon-carbon double bonds, carbon-carbon triple bonds, or a combination thereof, the method comprising adding to the composition a dye compound of the following formula:

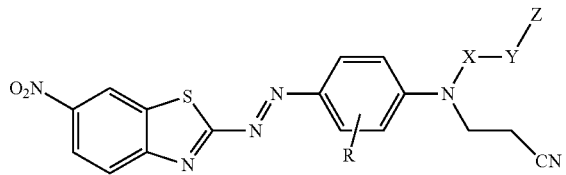

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, a terminal alkenyl, or a thiol,
in an amount sufficient to reduce a viscosity increase of the curable composition relative to a comparative composition that is the same as the curable composition except that it does not contain the dye compound.

* * * * *